United States Patent
Kim et al.

(10) Patent No.: US 12,133,545 B2
(45) Date of Patent: Nov. 5, 2024

(54) PLANT-SOAKED SOLUTION COMPRISING TAGATOSE, AND METHOD FOR PRODUCING SAME

(71) Applicant: CJ CHEILJEDANG CORPORATION, Seoul (KR)

(72) Inventors: Su Jeong Kim, Suwon-si (KR); Jung Gyu Park, Incheon (KR); Youn Kyung Bak, Suwon-si (KR); Sung Bae Byun, Sejong (KR); Seung Won Park, Yongin-si (KR); Dong Chul Jung, Seoul (KR); Jong Min Choi, Suwon-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 194 days.

(21) Appl. No.: 16/344,352

(22) PCT Filed: Jun. 23, 2017

(86) PCT No.: PCT/KR2017/006638
§ 371 (c)(1),
(2) Date: Apr. 23, 2019

(87) PCT Pub. No.: WO2018/079977
PCT Pub. Date: May 3, 2018

(65) Prior Publication Data
US 2019/0269164 A1    Sep. 5, 2019

(30) Foreign Application Priority Data
Oct. 31, 2016    (KR) .................. 10-2016-0142789

(51) Int. Cl.
*A23L 29/30*       (2016.01)
*A23L 21/12*       (2016.01)
*A23L 33/11*       (2016.01)
*A61K 36/736*     (2006.01)
*A61K 47/26*       (2006.01)
*A61P 3/08*         (2006.01)

(52) U.S. Cl.
CPC ............. *A23L 29/30* (2016.08); *A23L 21/12* (2016.08); *A23L 33/11* (2016.08); *A61K 36/736* (2013.01); *A61K 47/26* (2013.01); *A61P 3/08* (2018.01); *A23V 2002/00* (2013.01)

(58) Field of Classification Search
CPC .................. A23L 29/30; A23L 33/11
See application file for complete search history.

(56) References Cited

U.S. PATENT DOCUMENTS

| | | | |
|---|---|---|---|
| 6,432,464 B1 | 8/2002 | Andersen | |
| 9,125,409 B2 * | 9/2015 | Ohara | A01N 43/16 |
| 2006/0013925 A1 * | 1/2006 | Bauman | A23L 19/03 |
| | | | 426/102 |
| 2008/0045587 A1 | 2/2008 | Schur | |
| 2012/0004099 A1 * | 1/2012 | Kurahashi | A01N 43/78 |
| | | | 504/100 |
| 2012/0207910 A1 | 8/2012 | Lee | |
| 2016/0143333 A1 | 5/2016 | Cox | |

FOREIGN PATENT DOCUMENTS

| | | | |
|---|---|---|---|
| CN | 103783584 A | 5/2014 | |
| CN | 104055179 A | 9/2014 | |
| JP | 2009-286703 A2 | 12/2009 | |
| KR | 10-2001-0033864 A | 4/2001 | |
| KR | 10-2007-0071031 A | 7/2007 | |
| KR | 10-1134542 B | 4/2012 | |
| KR | 1230972 B1 * | 2/2013 | |
| KR | 10-2015-0083586 A | 7/2015 | |
| WO | WO-0113727 A1 * | 3/2001 | A01N 37/40 |
| WO | WO-2010021121 A1 * | 2/2010 | A01N 43/16 |
| WO | WO 2011-052967 A | 5/2011 | |

OTHER PUBLICATIONS

Yamada et al. Environ. Control Biol., 52 (3), 155-160. (Year: 2014).*
Imahori et al. Postharvest Biology and Technology 49 (2008) 54-60. (Year: 2008) (Year: 2008).*
Ko et al. Journal of Life Science. Mar. 2010, 20(3): 424-429. abstract (Year: 2010).*
Kim et. al. (HighProductionofD-Tagatose,aPotentialSugarSubstitute, Using ImmobilizedL-Arabinoselsomerase, Biotechnol. Prog. 2001, 17, 208-210) (Year: 2010).*
KR-1230972-B1 translated doc (Year: 2013).*
Mary Courtney Moore, "Drug evaluation: tagatose in the treatment of type 2 diabetes and obesity", Current Opinion In Investigational Drugs, 2006, vol. 7, No. 10, pp. 924-935.
Noriko Hayashi, "Features and use of syrup containing rare sugar", Monthly Food Chemical, 2015, vol. 9, pp. 66-71.
Use rare sugar Ginger syrup, Cookpad, https://cookpad.com/recipe/2694490, Jul. 2, 2014.
Candied Lemon & Lemon Syrup, Cookpad, https://cookpad.com/recipe/1213443, Aug. 19, 2010.
http://blog.naver.com/1979sujinlee/220039035525, Jun. 23, 2014, Home-made Prunus mume-soaked solution at Beksul cooking studio.
http://blog.naver.com/skfk1903/220848861014, Oct. 30, 2016, The healthy sweets with Beksul sweetree allulose and Beksul sweetree tagatose.
Tagatose, https://blog.naver.com/i06351/220128305807, Sep. 21, 2014. (This post relates to a method for producing a grapefruit-soaked solution using tagatose as a saccharide, in which the weight ratio of grapefruit to tagatose is 600g to 454g.).

(Continued)

Primary Examiner — Terry A McKelvey
Assistant Examiner — Jacob A Boeckelman
(74) Attorney, Agent, or Firm — Morgan, Lewis & Bockius LLP

(57) ABSTRACT

The present application relates to a plant-soaked solution comprising sugars containing tagatose and to a method for producing same.

11 Claims, 3 Drawing Sheets

(56) References Cited

OTHER PUBLICATIONS

Homemade 'Fruit-Soaked Solution' is a healthy 'Anti-Stress Medicine', http://www.koreadaily.com/news/read.asp?art_id=4038505, Feb. 19, 2016. (This article relates to a fruit-soaked solution and includes recommendations for making it using tagatose and xylose sugar that are low in calories.).

Zhirong Gan, "Four Seasons Healthy Fruit and Vegetable Diet Illustration", Sep. 30, 2015, Xinjiang People's Medical Publishing House (together with the English translation of the part cited in the Office Action).

* cited by examiner

[FIG. 1A]
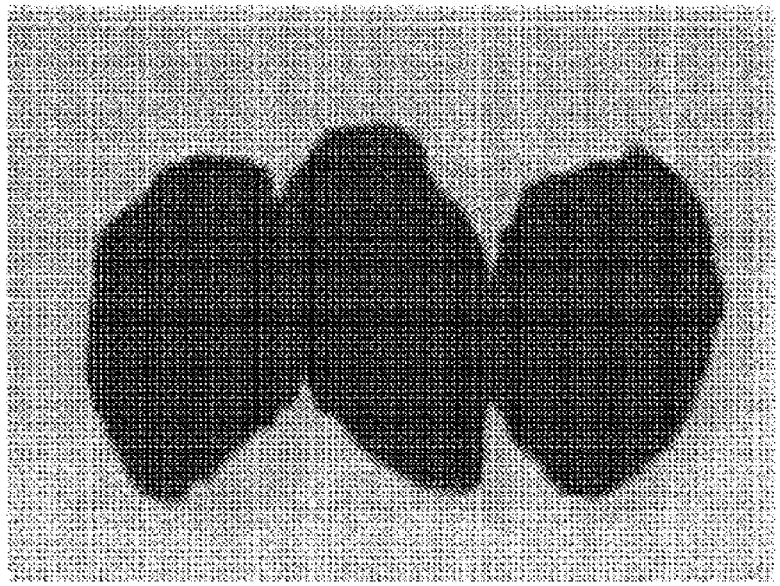
[FIG. 1B]
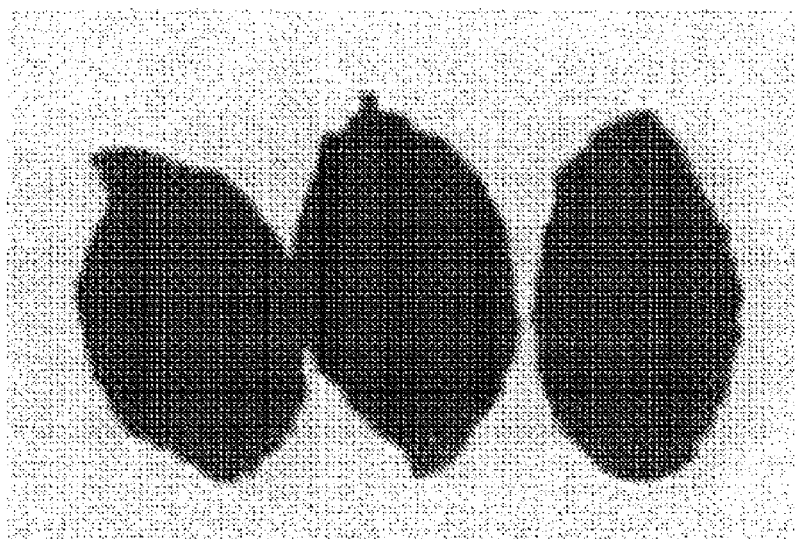

[FIG. 2]
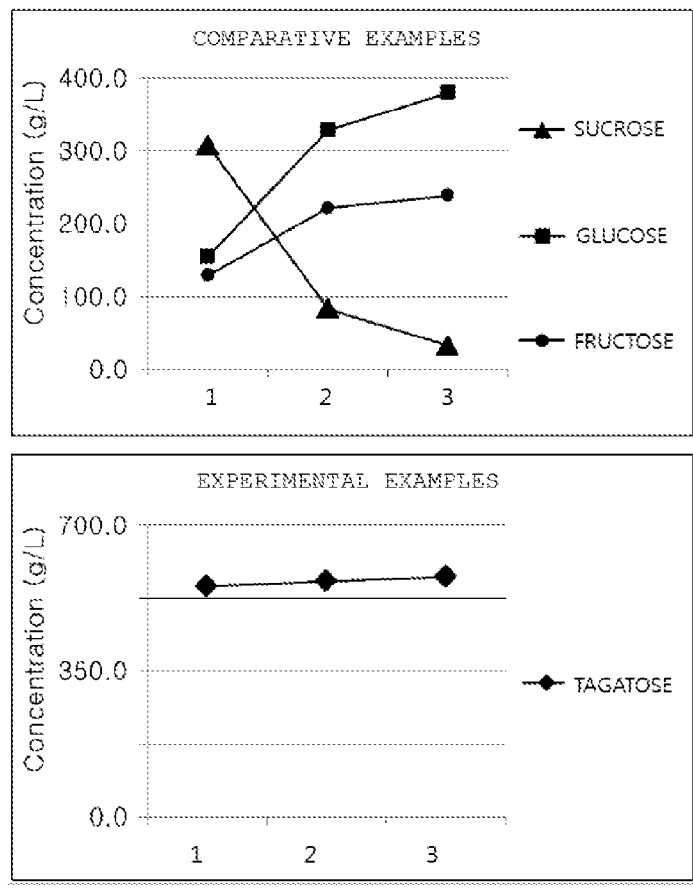
[FIG. 3]
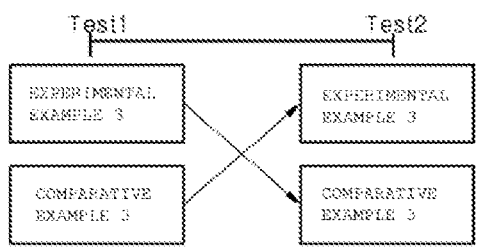
[FIG. 4]
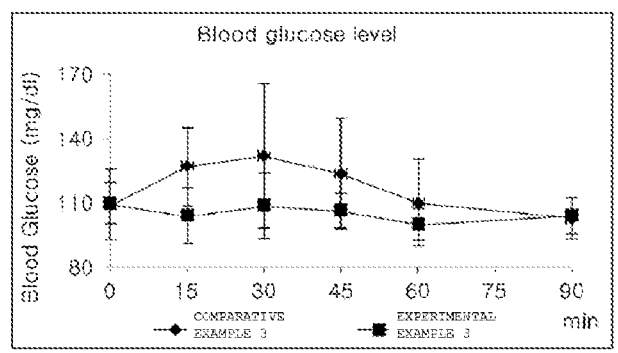

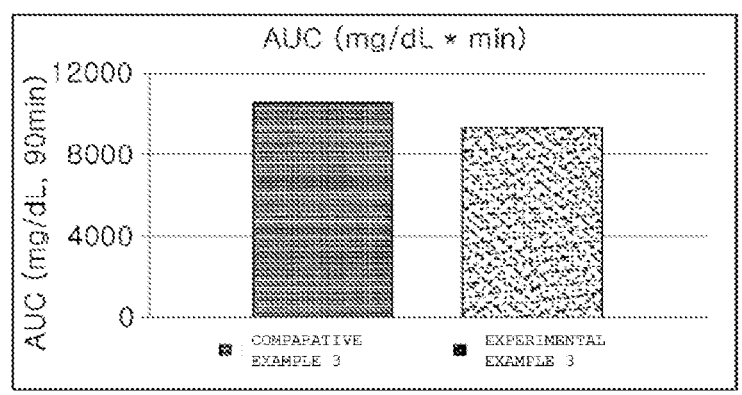

PLANT-SOAKED SOLUTION COMPRISING TAGATOSE, AND METHOD FOR PRODUCING SAME

TECHNICAL FIELD

Cross-Reference to Related Applications

This application claims the benefit of Korean Patent Application No. 10-2016-0142789, filed on Oct. 31, 2016, in the Korean Intellectual Property Office, the disclosure of which is incorporated herein in its entirety by reference.

TECHNICAL FIELD

The present invention relates to a plant-soaked solution comprising tagatose and a preparation method thereof.

BACKGROUND ART

"Soaked solution" is a food prepared by mixing a raw material for soaking with saccharide and maintaining soaking for a certain period of time so as to extract components present in the raw material for soaking into the saccharide. The soaked solution is ingested with no change, or diluted and drunk as a drink, or used for a marinade or a sauce.

Conventionally, the saccharide used for the preparation of the soaking solution is sucrose. Since sucrose is in a solid state, it takes a long time to dissolve. In addition, to mix sucrose and the raw material for soaking is accompanied by the labor of consumers and thus, there was the inconvenience. In addition, there was a disadvantage in that the soaked solution prepared using sucrose contains a large amount of monosaccharaides (such as glucose and fructose) which are the products of sucrose decomposition, and thus, when consumed, it causes a rapid rise in blood glucose and calories.

Tagatose is an isomer of galactose and is known as one of natural low-calorie saccharides. Tagatose exhibits very similar sweetness to sucrose, namely, is about 92% as sweet as sucrose and its calories per gram is 1.5 kcal, that is only about 38% of the calories per gram of sucrose (4.0 kcal/g). Its glycemic index (GI) is 3, that is only about 5% that of sucrose. For these reasons, tagatose has been a highly favored sucrose substitute. However, there has been no report on whether tagatose can be substituted for sucrose in soaking.

Under these circumstances, the present inventors have conducted extensive studies and made extensive efforts to develop a material that can substitute for sucrose in the preparation of a soaked solution. As a result, the present inventors found out that when the soaked solution was prepared using tagatose, the same level of useful components could be extracted from the raw material for soaking as the level in a conventional soaked solution prepared using sucrose so as to embody a soaked solution. Furthermore, the present inventors also found out that when tagatose was used in the preparation of the soaked solution, unlike sucrose, it did not decompose to glucose or fructose, so that the functionality of itself and low calorie can be maintained, thereby completing the present invention.

DISCLOSURE OF THE INVENTION

Technical Problem

An aspect of the present invention provides a plant-soaked solution comprising saccharide containing tagatose.

Another aspect of the present invention provides a preparation method of a plant-soaked solution, comprising a step of adding saccharide containing tagatose to a plant.

Hereinafter, the present invention is described in more detail. The contents not described in this specification can be sufficiently recognized and inferred by those skilled in the art or similar fields of the present application, and thus, the description thereof will be omitted.

Technical Solution

According to an aspect of the present invention, there is provided a plant-soaked solution comprising saccharide containing tagatose.

The term "soaked solution" in the present invention means a liquid food prepared by mixing a raw material for soaking with saccharide and maintaining soaking for a certain period of time so as to extract components present in the raw material for soaking.

According to an embodiment of the present invention, 33 to 67 parts by weight of the saccharide containing tagatose of the present invention may be contained based on 100 parts by weight of the soaked solution of the present invention. Specifically, 33.3 to 66.7 parts by weight, 44 to 55 parts by weight, 44.4 to 54.5 parts by weight, 48 to 52 parts by weight, or 50 parts by weight of the saccharide containing tagatose of the present invention may be contained based on 100 parts by weight of the soaked solution of the present invention.

According to another embodiment of the present invention, 1 to 100 parts by weight of the tagatose of the present invention may be contained based on 100 parts by weight of the saccharide containing tagatose of the present invention, based on dry solids. Specifically, 10 to 100 parts by weight, 15 to 100 parts by weight, 30 to 100 parts by weight, 50 to 100 parts by weight, 70 to 100 parts by weight, 90 to 100 parts by weight, 95 to 100 parts by weight, 99 to 100 parts by weight, or 99.5 to 100 parts by weight of the tagatose of the present invention may be contained based on 100 parts by weight of the saccharide containing tagatose of the present invention, based on dry solids. The tagatose used in the present invention may be, but not limited to, one directly extracted from natural products or one produced by chemical synthesis or biological methods.

According to another embodiment of the present invention, the saccharide containing tagatose of the present invention may further comprise, other than tagatose, one or more saccharide selected from the group consisting of monosaccharides, disaccharides, oligosaccharides, sugar alcohols, high intensity sweeteners, and liquid saccharide.

The term "monosaccharide" in the present invention means a basic unit of carbohydrate having the simplest structure which cannot be hydrolyzed by acids, bases, enzymes, etc. any more. Specifically, the monosaccharide of the present invention may be arabinose, xylose, fructose, allulose, allose, glucose, or galactose.

The term "disaccharide" in the present invention means a carbohydrate in which two monosaccharides are combined. Specifically, the "disaccharide" of the present invention may be sucrose, lactose, maltose, trehalose, turanose, or cellobiose.

The term "oligosaccharide" in the present invention means a carbohydrate in which 3 to 15 monosaccharides are combined. Specifically, the oligosaccharides of the present invention may be fructooligosaccharides, isomaltooligosaccharides, xylooligosaccharides, gentiooligosaccharides, maltooligosaccharides, or galactooligosaccharides.

The term "sugar alcohol" in the present invention means a compound in which the carbonyl group of saccharide is reduced. Specifically, the sugar alcohol of the present invention may be erythritol, xylitol, arabitol, mannitol, sorbitol, maltitol, or lactitol.

"high intensity sweetener" in the present invention means a sweetener having the sweetness ten times or more higher than that of sucrose. Specifically, the high intensity sweetner of the present invention may be aspartame, acesulfame K, rebaudioside A, or sucralose.

The term "liquid saccharide" in the present invention means a saccharide in liquid form. For example, the liquid saccharide of the present invention may include, but is not limited to, starch syrup, honey, maple syrup, agave syrup, and the like.

According to another embodiment of the present invention, the saccharide of the present invention may not contain sucrose.

The term "plant" in the present invention means green plants which have cell wall and chlorophyll, and photosynthesize and feed autotrophically. The plant of the present invention may include parts of the plant (e.g., fruits, leaves, stems, and roots of the plant).

According to another embodiment of the present invention, the plant of the present invention may be a fruit, vegetable, or wild grass.

The term "fruit" in the present invention means a fruit of a woody plant, which can be eaten by human.

Specifically, the fruit of the present invention may be one or more fruits selected from the group consisting of plum (*Prunus mume*), citrus, lemon, citron, grapefruit, lime, quince, *schizandra, rubus coreanus*, pear, apple, grape, mulberry, blueberry, mango, peach, plum (*Prunus salicina*), apricot, sweet persimmon, banana, and jujube. More specifically, the fruit of the present invention may be *Prunus mume* or lemon.

The term "vegetable" in the present invention means a herbaceous cultivated plant that can be eaten by human. Specifically, the vegetable of the present invention may be one or more vegetables selected from the group consisting of ginger, onion, red pepper, garlic, radish leaves, balloon flower roots, tomato, strawberry, oriental melon, melon, watermelon, and cucumber.

The term "wild grass" in the present invention means a herbaceous non-cultivated plant that grows in a mountain or field and can be eaten by human. Specifically, the wild grass of the present invention may be one or more wild grasses selected from the group consisting of mugwort, dandelion, plantain, purslane, and arrowroot.

According to another embodiment of the present invention, the *Prunus mume*-soaked solution of the present invention may further comprise polyphenol.

According to another embodiment of the present invention, the soaked solution of the present invention may be a health functional food for blood glucose regulation. Specifically, the blood glucose regulation may be the inhibition of blood glucose elevation.

According to yet another embodiment of the present invention, the *Prunus mume*-soaked solution of the present invention may be a health functional food for antioxidation.

The plant-soaked solution of the present invention may further include food ingredients other than tagatose, for example, vitamins, electrolytes, flavors, colorants, pectic acid and salts thereof, alginic acid and salts thereof, organic acids, protective colloid thickeners, pH adjusters, stabilizers, preservatives, glycerin, carbonating agents, and the like.

According to another aspect of the present invention, there is provided a preparation method of a plant-soaked solution, comprising a step of adding saccharide containing tagatose to a plant.

According to an embodiment of the present invention, 50 to 200 parts by weight of the saccharide containing tagatose of the present invention may be added based on 100 parts by weight of the plant of the present invention. Specifically, 80 to 120 parts by weight, 90 to 110 parts by weight, 95 to 105 parts by weight, or 100 parts by weight of the saccharide containing tagatose of the present invention may be added based on 100 parts by weight of the plant of the present invention.

According to an embodiment of the present invention, the saccharide containing tagatose or tagatose may be in crystalline form.

According to another embodiment of the present invention, the preparation method of the present invention may further comprise, after the step of adding saccharide containing tagatose to the plant of the present invention, a step of storing the resulting product of the step at temperature between 0° C. and 25° C. Specifically, the temperature may be between 0° C. and 20° C., between 0° C. and 15° C., between 0° C. and 10° C., between 0° C. and 5° C., between 3° C., and 25° C., between 3° C. and 20° C., between 3° C. and 15° C., between 3° C. and 10° C., between 3° C. and 5° C., or at 4° C. In addition, according to another embodiment of the present invention, the storage period of the present invention may be between 15 days and 6 months, between 15 days and 4 months, between 1 month and 6 months, between 1 month and 4 months, or between 1 month and 3 months.

According to another embodiment of the present invention, the preparation of the present invention may further comprise, before or after the step of adding saccharide containing tagatose to the plant of the present invention, a step of adding one or more saccharide selected from the group consisting of monosaccharides, disaccharides, oligosaccharides, sugar alcohols, high intensity sweeteners, and liquid saccharide, other than tagatose.

According to another embodiment of the present invention, the preparation of the present invention may further comprise, after the step adding saccharide containing tagatose to the plant of the present invention, a step of further adding a new plant which is the same as the plant of the present invention to the resulting product of the step, and then adding new saccharide which are the same as the saccharide containing tagatose of the present invention.

In addition, according to another embodiment of the present invention, the preparation of the present invention may not include a step of adding sucrose, fructose, glucose, or combinations thereof.

Descriptions of the saccharide containing tagatose, the tagatose, the plant, and the soaked solution, described in the plant-soaked solution, which is an aspect of the present invention described above, may be applied equally to the preparation method of the plant-soaked solution of the present invention. Therefore, in order to avoid the complexity of the specification of the present application, the description of overlapping parts is omitted.

Advantageous Effects

The soaked solution according to the present invention contains useful components of the same level as the level of a conventional soaked solution prepared using sucrose, and can maintain the functionality of tagatose itself and low calorie since the decomposition of tagatose into glucose or fructose is not achieved, and thus, can be substituted for conventional soaked solution prepared using sucrose.

BRIEF DESCRIPTION OF THE DRAWINGS

FIG. 1 is photographs of tissues of Prunus mumes soaked; FIG. 1A shows the tissue of Prunus mume steeped in sucrose for 3 months; and FIG. 1B shows the tissue of Prunus mume steeped in tagatose for 3 months.

FIG. 2 is a graph showing changes in the contents of tagatose and free saccharides (sucrose, glucose, and fructose) in the soaked solutions prepared using sucrose and tagatose, respectively.

FIG. 3 is a diagram illustrating an example of a randomized cross-over design study.

FIG. 4 is a graph comparing the blood glucose value results of Comparative example 3 with those of Experimental example 3.

FIG. 5 is a graph comparing the AUC result of Comparative example 3 with that of Experimental example 3.

MODE FOR CARRYING OUT THE INVENTION

The present invention will be described in detail with reference to the following Examples, but the following Examples are provided by way of illustration, and the present invention is not limited thereto.

Preparation Example 1: Preparation of Prunus mume-Soaked Solution Using Tagatose Domestic Prunus mume (green mumes) were washed cleanly with distilled water and allowed to dry naturally for one day. Then, stems were removed and 0.95 kg was added to a soaking vessel (glass material, capacity 5 kg) which was heated in boiling water at 100° C. for 10 minutes and naturally dried. Thereafter, 0.95 kg of tagatose (crystalline form, purity of 99% or more, CJ CheilJedang) was added, and the same amount of Prunus mumes and the same amount of tagatose were added in serial order one more time. Thereafter, the resulting products were maintained for 1 month, 2 months, and 3 months in a cold dark place condition (4° C., light-blocked condition, Korean food code), and then filtered with a sieve (8 mesh). The remaining original liquid was collected to prepare Prunus mume-soaked solutions [Experimental example 1 (maintenance for 1 month), Experimental example 2 (maintenance for 2 months) and Experimental example 3 (maintenance for 3 months)].

Preparation Example 2: Preparation of Lemon-Soaked Solution Using Tagatose

Lemon was washed with baking soda, and then, washed with distilled water to remove residual pesticide on the surface of lemon, and dried naturally for one day, and then sliced to a thickness of 0.5 to 2 cm, and seed was removed. 400 g of the resulting lemon was added to a a soaking vessel (glass material, capacity 1 kg) in the same manner as in Preparation example 1, and then 400 g of tagatose was added, and the same amount of lemon and the same amount of tagatose were added in serial order one more time. Thereafter, the resulting product was maintained for 15 days under cold dark condition (4° C., light-blocked condition, Korean food code), and then filtered with a sieve (8 mesh). The remaining original liquid was collected to prepare lemon-soaked solution (Experimental example 4).

Preparation Example 3: Preparation of Prunus mume-Soaked Solution and Lemon-Soaked Solution Using Sucrose Prunus mume-soaked solutions [Comparative example 1 (maintenance for 1 month), Comparative example 2 (maintenance for 2 months), and Comparative example 3 (maintenance for 3 months)] and lemon-soaked solution were prepared in the same manner as in Preparation examples 1 and 2 by substituting sucrose (crystalline-type white sucrose, CJ CheilJedang) for tagatose.

Example 1: Evaluation of Prunus mume-Soaked Solution 1-1. Evaluation of Tissue Change In the production of the Prunus mume-soaked solution, the moisture in the original material of Prunus mume is drained from the inside to outside of the tissue by the osmosis principle so that the tissue contracts. Therefore, it is usually judged that the more tissue of soaked Prunus mume contracts, the further the soaking progresses. Thus, changes in Prunus mume tissues after 3 months from the start of soaking in Preparation example 1 and Preparation example 3 were visually observed.

As a result, it was found that the tissue of the soaked Prunus mume of Preparation example 1 (FIG. 1B) contracted at the same level as the level of the soaked Prunus mume of Preparation example 3 (FIG. 1A) (FIG. 1).

1-2. Evaluation of Physical Properties (Solid Content, pH, and T-Color) of Soaked Solution In order to verify whether the soaking is carried out at the same level as in the Prunus mume-soaked solution using sucrose when tagatose is used for preparation of Prunus mume-soaked solution, physical properties (solid content, pH, and T-color) of Comparative examples 1, 2, and 3, and Experimental examples 1, 2, and 3 were measured and compared.

Specifically, the solid content (g content of solids dissolved in 100 g of soaked solution) was measured using a refractometer (ATAGO, Automatic Digital Refractometer RX-5000a); the pH was measured with a digital pH meter (METTLER TOLEDO, SEVEN COMPACT with InLab® Viscous Pro pH); and 1 cm cells were filled with Experimental examples 1, 2, and 3, and Comparative examples 1, respectively, and then the T-color (transmission color) was measured at a wavelength of 420 nm using a spectrophotometer (HITACHI, Double Beam Spectrophotometer U-2900) calibrated with distilled water. Statistical analysis was performed using SAS 9.1 program (SAS Inc., Cary, NC, USA) and the results were analyzed using the t-test method. All analyses were tested at the significance level of $p<0.05$.

As a result, there was no significant difference in Brix %, pH, and T-color, respectively, between Experimental examples 1, 2 and 3, and Comparative examples 1, 2 and 3 (Table 1). As for the solid content, like the conventional soaked solution, 50 Brix % or more was exhibited. The pH and T-color were not statistically significantly different between Experimental examples and Comparative examples (on the basis of 95% significance probability, $p>0.05$).

As a result, it could be found out that when the Prunus mume-soaked solution was prepared using tagatose, the soaked solution of the same level, in terms of physical properties, as the Prunus mume-soaked solution using sucrose, was embodied.

TABLE 1

| Solid content (Brix %) | | | pH | | | T-color (%) | | |
|---|---|---|---|---|---|---|---|---|
| Comparative example 1 | Comparative example 2 | Comparative example 3 | Comparative example 1 | Comparative example 2 | Comparative example 3 | Comparative example 1 | Comparative example 2 | Comparative example 3 |
| 57.20 | 57.55 | 56.50 | 2.62 | 2.54 | 2.65 | 83.15 | 80.10 | 49.90 |
| Experimental example 1 | Experimental example 2 | Experimental example 3 | Experimental example 1 | Experimental example 2 | Experimental example 3 | Experimental example 1 | Experimental example 2 | Experimental example 3 |
| 53.13 | 53.23 | 52.90 | 2.64 | 2.66 | 2.71 | 79.17 | 68.40 | 44.50 |

1-3. Determination of Citric Acid Content in the Soaked Solution

In order to verify whether the soaking is carried out at the same level as in the *Prunus mume*-soaked solution using sucrose and the useful components are extracted when tagatose is used for preparation of *Prunus mume*-soaked solution, the content of citric acid, which is one of main useful components of *Prunus mume*, in the *Prunus mume*-soaked solution was measured by high performance liquid chromatography (HPLC).

The test solution was prepared by placing 1 g of sample of Experimental examples 1, 2, and 3, and Comparative examples 1, 2, and 3, in a 50 mL constant volume flask, dissolving it in distilled water to adjust the total volume of the solution to 50 mL (20 g/L), and then filtering it through a 0.2 μm filter. The standard solution was prepared by placing 0.5 g of citric acid standard material (citric acid monohydrate, Sigma Aldrich) in a 50 mL constant volume flask, dissolving it in distilled water to adjust the total volume of the solution to 50 mL (10 g/L), diluting it to concentrations of about 0.3125 g/L, 0.625 g/L, 1.25 g/L, 2.5 g/L, 5 g/L and 10 g/L, and filtering it through a 0.2 μm filter.

The prepared test solutions and standard solutions were analyzed using HPLC (Alliance, Waters, e2695 Separation Modules, USA/Waters column Heater Module/RI detector Water 2414/Empower™ Software) under the conditions shown in Table 2 below.

TABLE 2

| Mobile phase | 5 mM $H_2SO_4$ |
|---|---|
| Column | 300 mm × 7.8 mm Amninex 87H (Bio Rad) |
| Flow rate | 0.6 mL/min |
| Temperature | 35° C. |
| Injection volume | 20 μL |
| Detector | DAD (Diode Array Detector) |

After HPLC analysis, a calibration curve was prepared with the citric acid content (g/L) as the abscissa axis and the area of the chromatogram as the ordinate axis. The citric acid areas Experimental examples 1, 2 and 3 and Comparative examples 1, 2 and 3 were read, and the citric acid contents were calculated from the calibration curve. As a result, it was found out that there was no significant difference in the contents of citric acid in Experimental examples 1, 2 and 3 and Comparative examples 1, 2 and 3, respectively (Table 3). As a result, it could be found out that when the solution was prepared using tagatose, the soaked solution of the same level, in terms of useful components, as the soaked solution using sucrose was embodied.

TABLE 3

| Citric acid content (g/L) | | |
|---|---|---|
| Comparative example 1 | Comparative example 2 | Comparative example 3 |
| 16.73 | 21.69 | 17.55 |
| Experimental example 1 | Experimental example 2 | Experimental example 3 |
| 18.25 | 19.82 | 16.08 |

1-4. Organoleptic Evaluation

Samples of Experimental example 3 and Comparative example 3 were diluted in lukewarm water at a ratio of 4:6, and each of the diluted samples was subjected to organoleptic evaluation by a trained panel of 17 evaluators for five preference attributes (flavor/color/sour taste/sweet taste/overall preference).

[Definition of Organoleptic Evaluation Terms]
1) Flavor preference: Personal preference for intrinsic flavor of soaked solution
2) Sweet taste preference: Personal preference for sweet taste
3) Sour taste preference: Personal preference for sour taste
4) Color preference: Personal preference for lightness and darkness of color of soaked solution
5) Overall preference: Overall personal preference As a result, it was found that color preference for Experimental example 3 was significantly higher than that for Comparative example 3, and other preference attributes except for color preference were similar (Table 4).

TABLE 4

| 5 point scale | Comparative example 3 | Experimental example 3 | p-value |
|---|---|---|---|
| Flavor preference | 2.6 | 2.5 | 0.234 |
| Sweet taste preference | 2.6 | 2.5 | 0.891 |
| Sour taste preference | 2.6 | 2.3 | 0.396 |
| Color preference | 1.9 | 2.8 | 0.001* |
| Overall preference | 2.4 | 2.2 | 0.425 |

*$p < 0.05$ 1-5. Determination of Tagatose Decomposition

In order to verify whether the calorie reduction effect of tagatose and the inherent functionality were maintained in the soaked solution prepared using tagatose, it was determined whether tagatose used in the preparation decomposed or not in the soaked solution.

Specifically, the contents of tagatose and free saccharides (sucrose, glucose, and fructose) in Experimental examples 1, 2, and 3, and Comparative examples 1, 2, and 3 were measured by using high performance liquid chromatography (HPLC). The test solution was prepared by placing 1 g of sample of Experimental examples 1, 2, and 3, and Comparative examples 1, 2, and 3, in a 50 mL constant volume flask, dissolving it in distilled water to adjust the total volume of the solution to 50 mL (20 g/L), and then filtering it through a 0.2 μm filter. The standard solutions were prepared by placing 1 g of each standard material, sucrose (SigmaS7903, CAS No. 57-50-1), glucose (SigmaG7528, CAS No. 50-99-7), fructose (SigmaF0127, CAS No. 57-48-7) and tagatose (Sigma75935, CAS No. 87-81-0) in a 50 mL constant volume flask, dissolving it in distilled water, diluting it to concentrations of about 0.625 g/L, 1.25 g/L, 2.5 g/L, 5 g/L, 10 g/L and 20 g/L, and filtering it through a 0.2 μm filter.

The prepared test solutions and standard solutions were analyzed using HPLC (Alliance, Waters, e2695 Separation Modules, USA/Waters column Heater Module/RI detector Water 2414/Empower™ Software) under the conditions shown in Table 5 below.

TABLE 5

| Mobile phase | Distilled water (HPLC Grade) |
|---|---|
| Column | 7.8 mm × 300 mm Amninex HPX87C (Bio Rad) |
| Flow rate | 0.6 mL/min |
| Temperature | 80° C. |
| Injection volume | 20 μL |
| Detector | Differential refractometer (RID: Refractive Index Detector) |

After HPLC analysis, a calibration curve was prepared with the contents of tagatose and free saccharides (sucrose, glucose, and fructose) (g/L) as the abscissa axis and the area of the chromatogram as the ordinate axis. The areas of tagatose and free saccharides of test solutions of Experimental examples 1, 2 and 3, and Comparative examples 1, 2 and 3 were read, and the contents of tagatose and free saccharides were obtained from the calibration curve (error range: ±5%).

As a result, it could be found that in Comparative example, sucrose decomposed into glucose and fructose, and in particular, in Comparative example 3, about 89.6% of the initial sucrose content at the soaking decomposed into glucose and fructose, but in all Experimental examples 1, 2, and 3, tagatose did not decompose and remained intactly (Table 6 and FIG. 2). Therefore, it could be found that in the conventional soaked solution prepared using sucrose, sucrose decomposed to glucose and fructose during the soaking period, which, when consumed, caused a rapid rise in blood glucose and provided high calorie (4 Kcal/g), but the soaked solution prepared using tagatose did not exhibit change in components during the soaking, and thus, could maintain the intrinsic calorie reduction effect (1.5 Kcal/g) and functionality of tagatose.

TABLE 6

| Sucrose content | | | Glucose content | | | Fructose content | | | Tagatose content | | |
|---|---|---|---|---|---|---|---|---|---|---|---|
| Comparative example 1 | Comparative example 2 | Comparative example 3 | Comparative example 1 | Comparative example 2 | Comparative example 3 | Comparative example 1 | Comparative example 2 | Comparative example 3 | Comparative example 1 | Comparative example 2 | Comparative example 3 |
| 30.8 | 8.4 | 3.2 | 15.4 | 33.0 | 38.0 | 13.0 | 22.1 | 24.0 | — | — | — |
| Experimental example 1 | Experimental example 2 | Experimental example 3 | Experimental example 1 | Experimental example 2 | Experimental example 3 | Experimental example 1 | Experimental example 2 | Experimental example 3 | Experimental example 1 | Experimental example 2 | Experimental example 3 |
| — | — | — | — | — | — | — | — | — | 55.3 | 56.7 | 57.7 |

(Unit: g/100 g of soaked solution)

1-7. Determination of Total Polyphenol Content in the Soaked Solution

In order to verify the functionality of *Prunus mume*-soaked solution, the content of polyphenol in the soaked solution was measured using Microplate Reader (Powerwave XS, BioTek, USA).

2% Sodium carbonate reagent is prepared by placing 2 g of sodium carbonate (Sigma 223484, CAS No. 497-19-8) in a 100 mL constant volume flask and adding distilled water thereto to adjust the total volume to 100 mL Folin-Ciocalteu's phenol reagent (Sigma F9252-1L) and distilled water were mixed at a ratio of 1:1 to prepare 50% Folin-Ciocalteu's phenol reagent. It was wrapped with aluminum foil to prevent light from being transmitted.

As for the test solutions, each of Experimental examples 1 to 3 and Comparative examples 1 to 3 was diluted with distilled water at a ratio of 1:1, and 0.1 mL of each solution was mixed with 0.1 mL of 50% Folin-Ciocalteu's phenol reagent and 2 mL of 2% sodium carbonate. Then, the test solutions were allowed to stand in a dark place for 30 minutes and absorbance was measured at 750 nm.

The standard solution was prepared by taking 0.4 g of gallic acid (Sigma G7384, CAS No. 149-91-7) in a 100 mL contant volume flask, adding distilled water thereto to adjust the total volume of the solution to 100 mL, and diluting the solution to concentrations of 31.25 ppm, 62.5 ppm, 125 ppm, 250 ppm and 500. The standard solution was mixed with the reagents in the same manner as the test solutions, and allowed to stand in a dark place for 30 minutes and then, absorbance was measured at 750 nm.

After the absorbance measurement, a calibration curve was prepared with the absorbance of the standard solution as the abscissa axis and the concentration of the standard solution as the ordinate axis. The total polyphenol content of each of Experimental examples 1 to 3 and Comparative examples 1 to 3 was calculated by using Equation 6 below.

$$\text{Total polyphenol content (mg/mL)} = (A \times B \times C)/D \quad \text{[Equation 1]}$$

*A: Total amount of test solution (mL), B: Dilution factor, C: Total polyphenol concentration in the test solution (mg/mL), D: Collected sample amount (mL)

As a result, it was found that the total polyphenol contents in Experimental examples 1 to 3 were significantly larger than those in Comparative Examples 1 to 3, which were stored for the same period of time (Table 7).

Therefore, it could be found that in the preparation of Prunus mume-soaked solution, by using tagatose rather than sucrose, the soaked solution of higher content of polyphenol can be prepared.

example 3 by about 10.9% (FIG. 5). Therefore, the intake of the soaked solution prepared using tagatose caused inhibition of the rapid rise in blood glucose, compared to the intake of the soaked solution prepared using sucrose, and thus, it was found that the intake of the soaked solution prepared using tagatose can help to inhibit the rapid rise in blood glucose after meals.

TABLE 8

| Classification | 0 min | 15 min | 30 min | 45 min | 60 min | 90 min |
|---|---|---|---|---|---|---|
| Comparative example 1 | 109.0 ± 16.6 | 126.8 ± 17.9 | 132.0 ± 33.7 | 123.3 ± 25.6 | 110 ± 20.2 | 102.5 ± 9.9 |
| Experimental example 1 | 109.5 ± 9.5 | 103.8 ± 13.0 | 108.5 ± 15.1 | 106.3 ± 8.0 | 99.8 ± 7.3 | 103.8 ± 8.3 |
| p-value | 0.932 | 0.008** | 0.087* | 0.163 | 0.229 | 0.391 |

*$p < 0.1$,
**$p < 0.05$

TABLE 7

| Classification | Comparative example 1 | Experimental example 1 | p value |
|---|---|---|---|
| Total polyphenol (mg/mL) | 0.45 | 0.67 | 0.023* |
| | Comparative example 2 | Experimental example 2 | p value |
| | 0.56 | 0.86 | 0.001* |
| | Comparative example 3 | Experimental example 3 | p value |
| | 0.52 | 0.73 | 0.000* |

*$p < 0.05$ 1-7. Effect of Inhibiting Blood Glucose Rise

In order to verify the health functionality of Experimental example 3, when Experimental example 3 and Comparative example 3 were consumed in a fasting state, changes in blood glucose were measured.

Four normal subjects with a fasting glucose level of less than 126 mg/dL were selected to participate in a randomized cross-over design study (FIG. 3). In the morning on the day of the experiment, Experimental example 3 or Comparative example 3 diluted with water at a ratio of 1:4 was taken in a fasting state. Changes in blood glucose were measured using a glucose meter (OptiumXceed Blood Glucose Monitoring System, Abbott Diabetes CreInc., USA) at the time points (0 minute, 15 minutes, 30 minutes, 45 minutes, 60 minutes, and 90 minutes).

In order to avoid a cross-over effect on the substance to be consumed, a wash-out period of one week was given, and Experimental example 3 or Comparative example 3 was taken in the same manner as above, and then, changes in blood glucose were measured and the area under the curve (AUC) was calculated by using the Trapezoidal Rule.

As a result, it was found that Experimental example 3 significantly inhibited the rise in blood glucose after 15 minutes of intake by about 18% compared to Comparative example 3, and inhibited the rise in blood glucose after 30 minutes by about 17.8% (Table 8 and FIG. 4). The AUC of Experimental example 3 was lower than that of Comparative Example 2: Evaluation of Lemon-Soaked Solution 2-1. Evaluation of Physical Properties (Solid Content, pH, and T-Color) of Soaked Solution In order to verify whether the soaking is carried out at the same level as in the lemon-soaked solution using sucrose when tagatose is used for preparation of lemon-soaked solution, physical properties (solid content, pH, and T-color) of Comparative example 4 and Experimental example 4 were measured and compared. The measurement methods of solid content, pH and T-color were the same as in Examples 1 to 2.

As a result, as for the solid content, like the conventional soaked solution, 50 Brix % or more was exhibited. The pH and T-color were not statistically significantly different between Experimental example and Comparative example (on the basis of 95% significance probability, $p>0.05$) (Table 9).

As a result, it could be found out that when the lemon-soaked solution was prepared using tagatose, the soaked solution of the same level, in terms of physical properties, as the lemon-soaked solution using sucrose, was embodied.

TABLE 9

| Classification | Solid content (Brix %) | pH | T-color (%) |
|---|---|---|---|
| Comparative example 4 | 59.51 | 3.38 | 82.21 |
| Experimental example 4 | 56.46 | 3.42 | 86.38 |

2-2. Determination of Tagatose Decomposition

In order to verify whether the low calorie of tagatose and the inherent functionality were maintained in the lemon-soaked solution prepared using tagatose, it was determined whether tagatose used in the preparation decomposed or not in the lemon-soaked solution.

Specifically, the contents of tagatose and free saccharides (sucrose, glucose, and fructose) in Experimental example 4 and Comparative example 4 were measured by using HPLC. The measurement method and HPLC analysis conditions were the same as those of Example 1-5.

As a result, it could be found that in Comparative example 4, sucrose decomposed to sucrose and fructose, but tagatose used in Experimental example 4 did not decompose and remained intactly (Table 10). Therefore, it could be found that as in Prunus mume-soaked solution, tagatose did not decompose also in lemon-soaked solution, and the lemon-soaked solution could maintain the intrinsic calorie reduction effect and functionality of tagatose.

TABLE 10

| Classification | Sucrose content | Glucose content | Fructose content | Tagatose content |
|---|---|---|---|---|
| Comparative example 4 | 49.4 | 3.6 | 3.1 | — |
| Experimental example 4 | — | — | — | 58.5 |

(Unit: g/100 g of soaked solution)

2-3. Determination of the Vitamin C Content in the Soaked Solution

In order to verify whether the soaking is carried out at the same level as in the lemon-soaked solution using sucrose and the useful components are extracted when tagatose is used for preparation of lemon-soaked solution, the content of vitamin C, which is one of main useful components of lemon, in the lemon-soaked solution was measured by high performance liquid chromatography (HPLC).

The test solution was prepared by placing 1 g of samples of Experimental example 4 and Comparative example 4, in a 50 mL constant volume flask, dissolving it in distilled water to adjust the total volume to 50 mL (20 g/L), and then filtering it through a 0.2 μm filter. The standard solution was prepared by placing 0.01 g of vitamin C standard material (L-Ascorbic acid, SigmaA5960, CAS No. 50-81-7) in a 10 mL constant volume flask, dissolving it in distilled water to adjust the total volume of the solution to 10 mL (0.1 g/L), diluting it to 5 points of concentrations of about 0.00625 g/L, 0.0125 g/L, 0.025 g/L, 0.05 g/L, 0.1 g/L, and filtering it through a 0.2 μm filter.

The prepared test solutions and standard solutions were analyzed using HPLC (Alliance, Waters, e2695 Separation Modules, USA/Waters column Heater Module/RI detector Water 2414/Empower™ Software) under the analytic conditions shown in Table 11 below.

TABLE 11 ®

| Mobile phase | Acetonitrile 90% + formic acid 10% |
|---|---|
| Column | 250 mm × 4.6 mm Intersil ® HPLC |
| Flow rate | 0.7 mL/min |
| Temperature | 35° C. |
| Injection volume | 10 μL |
| Detector | DAD (Diode Array Detector) |

After HPLC analysis, a calibration curve was prepared with the content of vitamin C (g/L) as the abscissa axis and the area of the chromatogram as the ordinate axis. The areas of vitamin C of test solutions of Experimental example 4 and Comparative example 4 were read by using the following equation, and the content of vitamin C was calculated from the calibration curve.

Vitamin C content (mg/100 g soaked solution) = [Equation 2]

$$\frac{\text{Concentration obtained from calibration curve (g/L)} \times \text{dilution volume (mL)} \times 100 \times 1000}{\text{Collected sample amount (g)} \times 1000}$$

As a result, it was found that the vitamin C content of Experimental example 4 and Comparative example 4 was not significantly different (Table 12). As a result, it could be found out that when the lemon-soaked solution was prepared using tagatose, the soaked solution of the same level, in terms of useful components, as the lemon-soaked solution using sucrose was embodied, too.

TABLE 12

| Classification | Vitamin C (mg/100 g soaked solution) |
|---|---|
| Comparative example 4 | 30.5 |
| Experimental example 4 | 29.6 |

The invention claimed is:

1. A plant-soaked solution composition comprising a plant and a saccharide containing tagatose, wherein the plant-soaked solution is obtained by:
   mixing a plant with saccharide containing tagatose; and
   soaking the plant with the saccharide containing tagatose for 15 days to 6 months to provide the plant-soaked solution composition,
   wherein the ratio of the saccharide containing tagatose: plant soaked solution is 33 to 67 parts by weight:100 parts by weight of the soaked solution,
   wherein the tagatose is present in an amount of 1 to 100 parts by weight:100 parts by weight of the saccharide containing tagatose, based on dry solids, and
   wherein the plant comprises fruit.

2. The plant-soaked solution composition of claim 1, wherein the saccharide does not contain sucrose.

3. The plant-soaked solution composition of claim 1, wherein the fruit comprises lemon.

4. The plant-soaked solution composition of claim 1, which is a health functional food for blood glucose regulation.

5. The plant-soaked solution composition of claim 3, which is a health functional food for antioxidation.

6. The plant-soaked solution composition of claim 1, wherein the fruit comprises plum.

7. The plant-soaked solution composition of claim 1, wherein the fruit comprises one or more fruits selected from the group consisting of *Prunus mume*, citrus, lemon, citron, grapefruit, lime, quince, *schizandra, rubus coreanus*, pear, apple, grape, mulberry, blueberry, mango, peach, *Prunus salicina*, apricot, sweet persimmon, banana, and jujube.

8. A method of preparing a plant-soaked solution, comprising
   Preparing the plant-soaked solution composition of claim 1,
   filtering the plant-soaked solution composition, and
   collecting the filtered solution, wherein the filtered solution is the plant-soaked solution.

9. The method of claim 8, wherein the plant-soaked solution further comprises polyphenol and the content of total polyphenol in the plant-soaked solution is 0.6 mg/ml or more.

10. The method of claim 8, wherein the plant-soaked solution contains at least 0.67 mg/ml polyphenol.

11. A method of extracting polyphenol from fruit in the plant-soaked solution composition of claim 1, comprising adding saccharide containing tagatose to the plant.

* * * * *